United States Patent
Lahiri et al.

(10) Patent No.: US 9,199,953 B2
(45) Date of Patent: Dec. 1, 2015

(54) AMORPHOUS FORM OF CABAZITAXEL AND PROCESS FOR ITS PREPARATION

(71) Applicant: FRESENIUS KABI ONCOLOGY LIMITED, New Delhi (IN)

(72) Inventors: Saswata Lahiri, Haryana (IN); Bhuwan Bhaskar Mishra, Haryana (IN); Vijay Ojha, Haryana (IN); Nilendu Panda, Haryana (IN); Sonu Prasad Shukla, Haryana (IN)

(73) Assignee: FRESENIUS KABI ONCOLOGY LIMITED, New Delhi (IN)

( * ) Notice: Subject to any disclaimer, the term of this patent is extended or adjusted under 35 U.S.C. 154(b) by 123 days.

(21) Appl. No.: 13/663,886

(22) Filed: Oct. 30, 2012

(65) Prior Publication Data

US 2013/0109870 A1    May 2, 2013

(30) Foreign Application Priority Data

Nov. 1, 2011    (IN) .......................... 3109/DEL/2011

(51) Int. Cl.
    *C07D 305/14*    (2006.01)
(52) U.S. Cl.
    CPC .................................. *C07D 305/14* (2013.01)
(58) Field of Classification Search
    CPC combination set(s) only.
    See application file for complete search history.

(56) References Cited

U.S. PATENT DOCUMENTS 5,847,170 A † 12/1998 Bouchard
9,012,886 B2 * 4/2015 Hwang et al. ................... 257/15

FOREIGN PATENT DOCUMENTS

| CN | 102659722 | 9/2012 |
| WO | 2012/142117 | 10/2012 |
| WO | 2012/142117 A1 † | 10/2012 |
| WO | 2013024495 A1 † | 2/2013 |

OTHER PUBLICATIONS

Dr Reddys Labs Ltd., "Amorphous Cabazitaxel and Process for its Preparation," IP.com Journal, Sep. 6, 2012 (entire document—5 pages).
U.S. Appl. No. 61/474,572, filed Apr. 12, 2011; Applicant is Simo et al.; earliest priority of WO 2012/142117.†

\* cited by examiner
† cited by third party

*Primary Examiner* — Sun Jae Yoo
(74) *Attorney, Agent, or Firm* — Occhiuti & Rohlicek LLP

(57) ABSTRACT

An amorphous form of cabazitaxel is disclosed. It is preferably characterized by an X-ray powder diffraction (XRD) pattern as depicted in FIG. 1. It is prepared by (a) preparing a solution of cabazitaxel in a suitable solvent and mixture thereof; and (b) recovering the amorphous forms of cabazitaxel from the solution by removal of the solvent.

7 Claims, 2 Drawing Sheets

AMORPHOUS FORM OF CABAZITAXEL AND PROCESS FOR ITS PREPARATION

FIELD OF THE INVENTION

The present invention relates to the amorphous form of 4-acetoxy-2α-benzoyloxy-5β,20-epoxy-1-hydroxy-7β,10β-dimethoxy-9-oxotax-11-en-13α-yl(2R,3S)-3-tert-butoxycarbonylamino-2-hydroxy-3-phenyl-propionate, i.e., cabazitaxel, methods for its preparation and pharmaceutical composition thereof.

BACKGROUND OF THE INVENTION

Cabazitaxel, chemically known as 4-acetoxy-2α-benzoyloxy-5β,20-epoxy-1-hydroxy-7β,10β-dimethoxy-9-oxotax-11-en-13α-yl(2R,3S)-3-tert-butoxycarbonylamino-2-hydroxy-3-phenyl-propionate, is represented by formula (I).

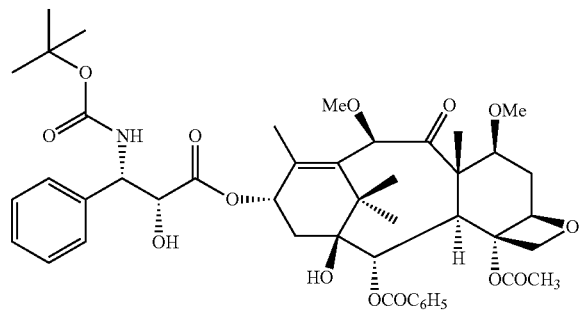

(I)

It is a microtubule inhibitor, indicated in combination with prednisone for treatment of patients with hormone-refractory metastatic prostate cancer previously treated with a docetaxel-containing treatment regimen, under the trade name Jevtana®.

Cabazitaxel is known from U.S. Pat. No. 5,847,170. The process for the preparation of cabazitaxel as described in U.S. Pat. No. 5,847,170 involves column chromatography, which is cumbersome, tedious and not commercially viable.

The acetone solvate of 4-acetoxy-2α-benzoyloxy-5β,20-epoxy-1-hydroxy-7β,10β-dimethoxy-9-oxotax-11-en-13α-yl(2R,3S)-3-tert-butoxycarbonylamino-2-hydroxy-3-phenyl-propionate (Form A) is formed by crystallization by using acetone and is characterized by X-ray diffraction in U.S. Pat. No. 7,241,907.

U.S. Patent Application Publication No. 2011/0144362 describes anhydrous crystalline Forms B to Form F, ethanolates Form B, D, E and F and mono and dihydrate forms of cabazitaxel. All of the anhydrous crystalline forms are prepared either from the acetone solvate or ethanol solvate. Mono and dihydrate forms are formed at ambient temperature in an atmosphere containing 10% and 60% relative humidity, respectively.

From the above mentioned references, it is evident that pure polymorphic forms of cabazitaxel prepared in the literature were prepared from solvates and not directly from cabazitaxel.

None of the literature reported earlier mentions the amorphous form of cabazitaxel. The present invention provides a novel form of cabazitaxel, i.e., amorphous cabazitaxel which is directly obtained from crude 1 cabazitaxel without formation of any solvate or hydrate of cabazitaxel.

SUMMARY OF THE INVENTION

In a first aspect, there is provided an amorphous form of cabazitaxel.

In a second aspect, there is provided a process for the preparation of an amorphous form of cabazitaxel comprising the steps of:
a) preparing a solution of cabazitaxel in a suitable solvent and mixture thereof; and
b) recovering the amorphous forms of cabazitaxel from the solution thereof by removal of the solvent.

In another aspect, there is provided a pharmaceutical composition that includes a therapeutically effective amount of an amorphous form of cabazitaxel and one or more pharmaceutically acceptable carriers, excipients or diluents.

BRIEF DESCRIPTION OF THE ACCOMPANYING DRAWINGS

Figure 1:
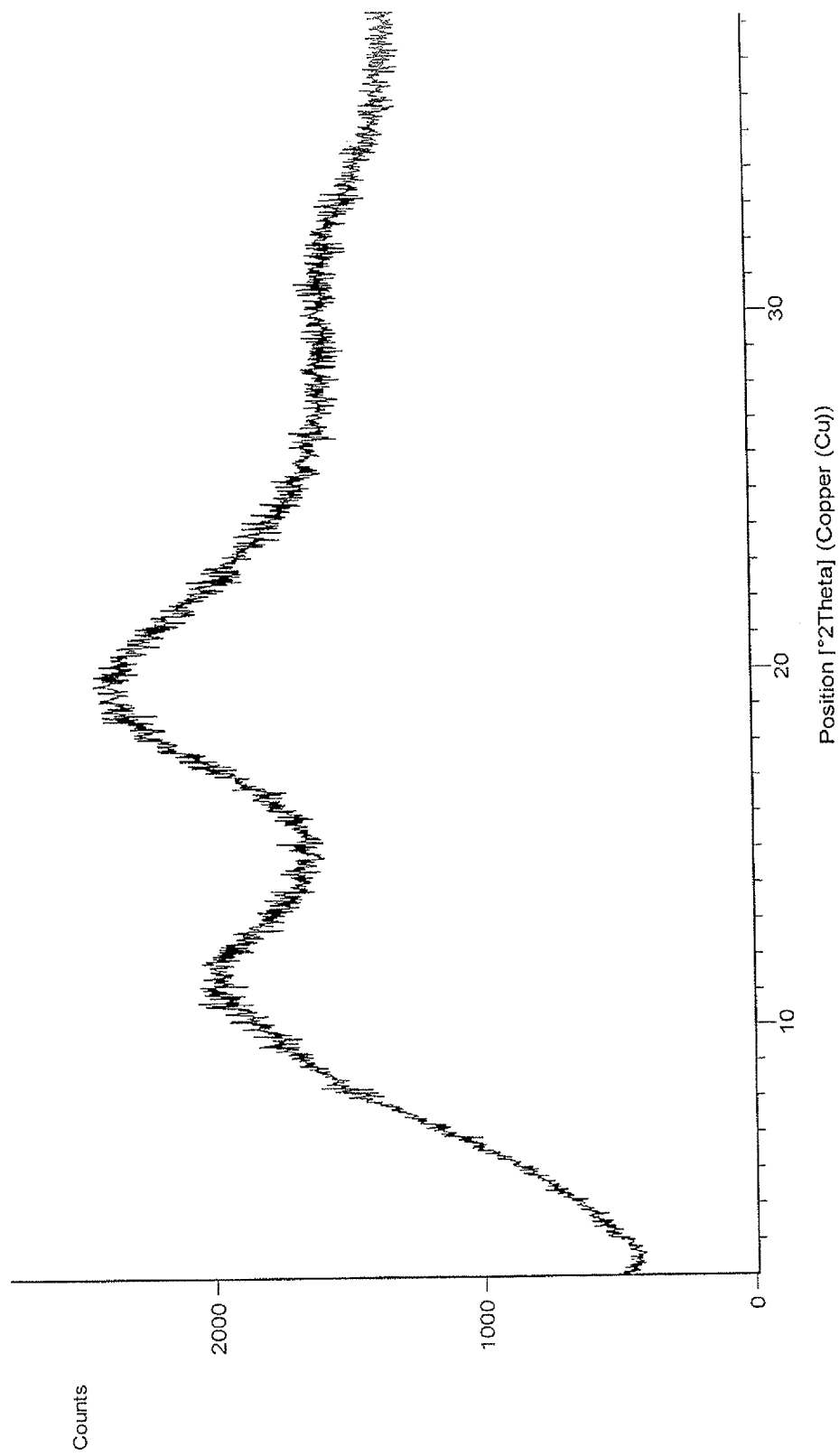

FIG. 1, which represents the X-ray (powder) diffraction (XRD) pattern of the amorphous form of cabazitaxel of the present invention.

Figure 2:
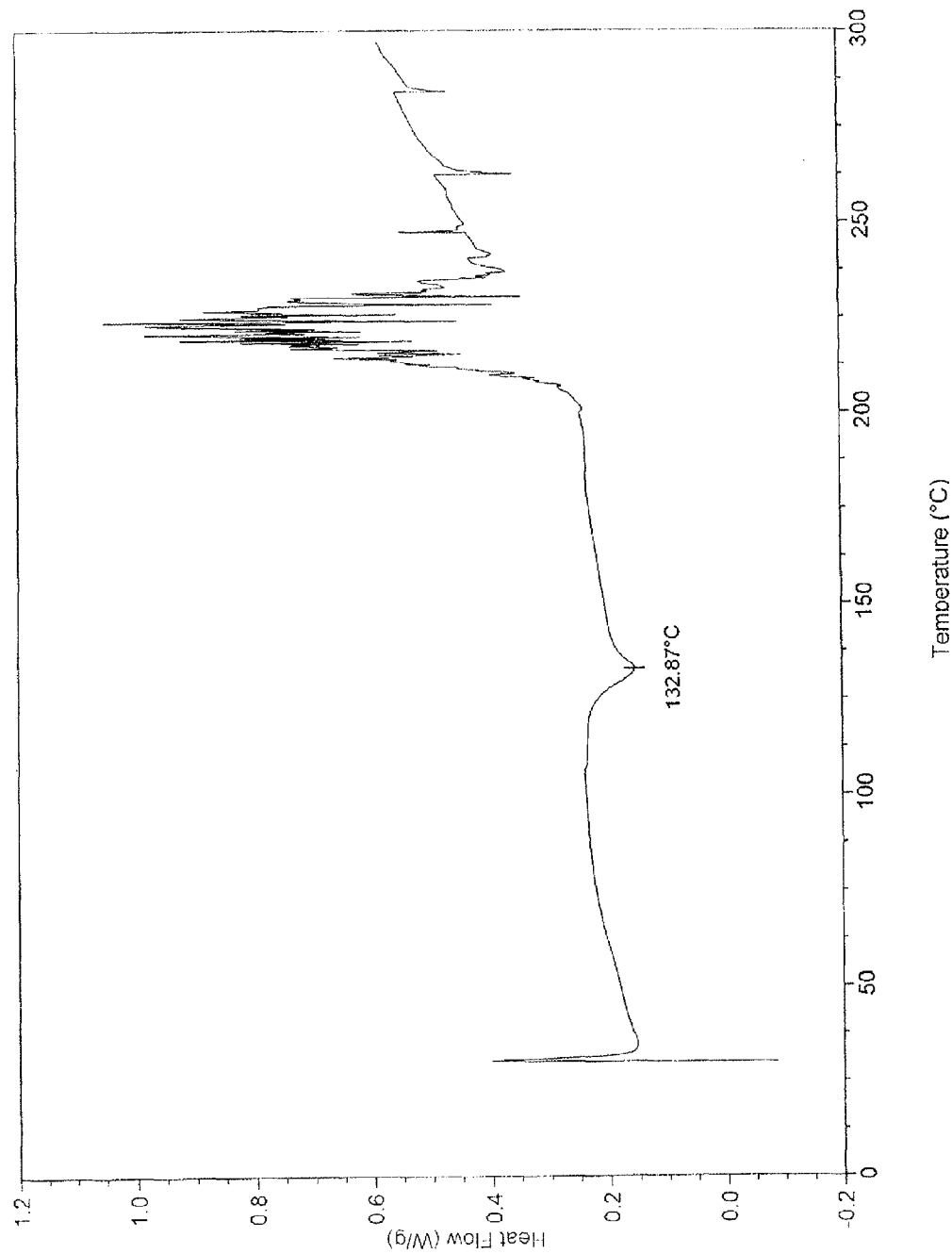

FIG. 2, which represents the Differential Scanning Calorimetry (DSC) analysis for the amorphous form of cabazitaxel of the present invention.

DETAILED DESCRIPTION OF THE INVENTION

The amorphous form of cabazitaxel may be characterized by XRD as depicted in FIG. 1.

The amorphous form of cabazitaxel is totally and completely devoid of any signal due to a crystalline form in its X-ray (powder) diffraction pattern.

4-acetoxy-2α-benzoyloxy-5β,20-epoxy-1-hydroxy-7β,10β-dimethoxy-9-oxotax-11-en-13α-yl(2R,3S)-3-tert-butoxycarbonylamino-2-hydroxy-3-phenyl-propionate, i.e., cabazitaxel used as starting material, may be prepared according to methods known in art, such as described in U.S. Pat. No. 5,847,170.

In general, the solution of cabazitaxel may be obtained by dissolving cabazitaxel in a suitable solvent.

The suitable solvent may be selected from the group comprising alcohols, such as methanol, ethanol and isopropanol; nitriles, such as acetonitrile; chlorinated hydrocarbons, such as methylene chloride and ethylene dichloride; esters, such as ethyl acetate and isopropyl acetate; cyclic ethers, such as dioxane and tetrahydrofuran and mixtures thereof. The most preferred solvent is methylene chloride.

The volume of the solvent that can be used in step a) depends on the polarity and the solubilizing capacity of the solvent and typically can be employed in the range of between 2 to 100 times by volume per gram of cabazitaxel.

The solution of cabazitaxel in a suitable solvent may be obtained at ambient temperature.

Removal of solvent may include one or more of the techniques of distillation, distillation under vacuum, evaporation, spray drying and freeze drying.

The temperature at which the solvent is removed depends on the solvent employed and generally can be from about 20° C. to about 200° C.

After evaporation of the solvent, the residual solid may optionally be treated with an organic solvent. The organic solvent may be selected from hydrocarbon solvents such as hexane, heptane, toluene and benzene.

The amorphous form of cabazitaxel may be recovered from the solution using a spray drying technique. A mini-Spray dryer (Model: Labultima (LU228) can be used. Labultima (LU228) Mini-Spray Dryer operates on the principle of nozzle spraying in a parallel flow, i.e., the sprayed product and the drying gas flow in the same direction. The drying gas can be air or an inert gas such as nitrogen, argon and carbon dioxide.

The air inlet temperature of the spray drier can be from about 40° C. to about 100° C.

After removal of the solvent, the process may include drying of the residual solid in a drying oven.

The resulting amorphous form of cabazitaxel may be formulated into ordinary dosage forms such as, for example, tablets, capsules, pills, solutions, etc. In these cases, the medicaments can be prepared by conventional methods with conventional pharmaceutical excipients. In addition to the common dosage forms set out above, the amorphous form of cabazitaxel may also be administered by controlled release means and/or delivery devices.

Further, the amorphous cabazitaxel described herein can be used in a method for treatment of hormone-refractory metastatic prostate cancer. The method of treatment includes administering to a mammal in need of treatment a dosage form that includes a therapeutically effective amount of the amorphous form of cabazitaxel.

The methods for the preparation of the amorphous form of cabazitaxel of the present invention may be illustrated by way of the following examples, which in no way should be construed as limiting the scope of the invention.

Example 1

2.0 g of cabazitaxel was dissolved in 20 ml of dichloromethane and concentrated at 35-40° C. under vacuum to obtain a solid product. The product was further dried for 1 h at 35-40° C. under vacuum. Crude product was stirred with 40 ml n-hexane at room temperature for 15-20 min and filtered. The solid material obtained was washed with 40 ml n-hexane and dried for 6-7 hrs at 50-55° C. under reduced pressure.

Example-2

2.0 g of cabazitaxel was dissolved in 20 ml of dichloromethane. The solution was then filtered through 0.5 micron filter and filtrate was spray dried for 6 hrs at 40-45° C. to obtain amorphous cabazitaxel.

The invention claimed is:

1. A process for preparing an amorphous form of Cabazitaxel, wherein the Cabazitaxel is characterized by an X-ray powder diffraction (XRD) pattern as depicted in FIG. 1 and the process comprises: (a) preparing a solution of Cabazitaxel in a solvent selected from an alcohol, a nitrile, a chlorinated hydrocarbon, an ester, a cyclic ether, or a mixture thereof; and (b) recovering the amorphous form of Cabazitaxel from the solution by removal of the solvent or the mixture thereof.

2. The process of claim 1, wherein the solvent is a chlorinated hydrocarbon.

3. The process of claim 2, wherein the chlorinated hydrocarbon is dichloromethane.

4. The process of claim 1, wherein the amorphous form is recovered from the solution using a spray drying technique.

5. The process of claim 1, wherein the amorphous form is recovered by distillation, evaporation, or freeze drying.

6. The process of claim 1, further comprising step (c): (c) treating the amorphous form of Cabazitaxel with an organic solvent.

7. The process of claim 6, wherein the organic solvent is a hydrocarbon.

\* \* \* \* \*